US005152844A

United States Patent [19]

Wilwerding et al.

[11] Patent Number: 5,152,844

[45] Date of Patent: * Oct. 6, 1992

[54] DEGRADATION OF POLYCHLORINATED BIPHENYLS

[75] Inventors: Michael Wilwerding, 2327 Eberlien, Klamath Falls, Oreg. 97601; Robert Hoch, Hensonville, N.Y.

[73] Assignee: Michael Wilwerding, Klamath Falls, Oreg.

[ * ] Notice: The portion of the term of this patent subsequent to Jun. 5, 2007 has been disclaimed.

[21] Appl. No.: 513,653

[22] Filed: Apr. 24, 1990

Related U.S. Application Data

[63] Continuation-in-part of Ser. No. 341,316, Apr. 21, 1989, Pat. No. 4,931,167, which is a continuation of Ser. No. 108,190, Oct. 13, 1987, abandoned.

[51] Int. Cl.[5] .......................... C07C 1/30; C10G 17/00

[52] U.S. Cl. ...................................... 134/25.1; 134/28; 208/262.5; 210/909; 405/128; 405/263; 423/659; 423/DIG. 20; 585/469; 588/207

[58] Field of Search ........................ 423/659, DIG. 20; 134/25.1, 28; 208/262.5; 210/909; 405/128, 263; 585/469; 588/207; 71/63, 903

[56] References Cited

U.S. PATENT DOCUMENTS 3,832,306 8/1974 Hackett et al. ..................... 502/423
4,699,721 10/1987 Meenan et al. ..................... 423/481
4,931,167 6/1990 Wilwerding ................ 423/DIG. 20

*Primary Examiner*—Wayne Langel
*Attorney, Agent, or Firm*—Curtis, Morris & Safford

[57] ABSTRACT

Polychlorinated biphenyls are chemically degraded by contact with a Lewis acid catalyst in a nonaqueous liquid medium, in the presence of a cation which combines the chlorines on the PCBs to form a solid chloride of the cation which will precipitate out from the liquid medium. Preferred Lewis acids are metal halides, particularly a combination of aluminum chloride and ferric chloride, and the preferred cation is potassium in the form of potassium hydroxide. The process is susceptible to both batch and continuous operation. The process for chemically degrading PCBs with a Lewis acid catalyst can be applied to PCB-containing soils, sediments and sludges by contacting those materials, under anhydrous conditions, with Lewis acids and preferably with Lewis acids and a metal cation capable of reacting with the hydrohalogen released from the PCBs by the Lewis acids. The Lewis acids may be supplied to the process by the adventitious corrosion of a vessel containing the PCB-contaminated soil.

44 Claims, 3 Drawing Sheets

DEGRADATION OF POLYCHLORINATED BIPHENYLS

This application is a continuation in part of copending application Ser. No. 341,316 filed Apr. 21, 1989, now U.S. Pat. No. 4,931,167, which was a continuation of application Ser. No. 108,190, filed Oct. 13, 1987, now abandoned.

BACKGROUND OF THE INVENTION

This invention relates to the disposal of polychlorinated biphenyls, commonly known as PCBs. More particularly, this invention relates to processes for the detoxification of soils, sludges and sediments by degradation of PCBs contained therein into environmentally and toxicologically harmless compounds. Even more specifically this invention relates to methods for remediation of soils in an economically and technically advantageous method.

In their most common form, PCBs are mixtures of isomers of trichlorobiphenyl, tetrachlorobiphenyl, pentachlorobiphenyl, and small amounts of dichlorobiphenyl and hexachlorobiphenyl. Up until the early 1970's PCBs were used in a wide range of applications due to their unique blend of fire resistance, thermal and oxidative stability, electrical characteristics, solvency, inertness and liquid range. Some of their most important uses were as follows: as a dielectric medium in transformers, either alone or in blends with other materials such as trichlorobenzene; as the dielectric impregnating medium in capacitors; as plasticizers; as ingredients in lacquers, paints and varnishes and adhesives; as water proofing compounds in various types of coatings; as lubricants or lubricant additives under extreme conditions; as heat transfer fluids; as fire resistent hydraulic fluids; as vacuum pump fluids; and as air compressor lubricants. Their largest application was in the electrical industry as a dielectric medium in transformers and capacitors.

In the late '60's and early '70's, it was discovered that PCBs have a major potential for environmental contamination due to their extremely slow biodegradation rates. The persistence and toxicity of PCBs have prompted governmental action restricting their use and application, and the Toxic Substance Control Act of 1976 contained provisions for discontinuance of their use and for their eventual disposal. Even trace amounts of PCBs are considered undesirable.

Current regulations issued by the Environmental Protection Agency specify incineration as the only acceptable method of PCB disposal in the absence of special clearance. Incineration, of course, is expensive and hazardous, and in cases where the PCBs are a minor component mixed in with a nonprohibited fluid such as one of the various types of replacement dielectric fluids, one loses the nonprohibited fluid as well by incinerating the entire mixture.

Methods for remediating soils, sediments and sludges include incineration, solvent extraction, chemical treatment and other processes. Each of these prior art methods has its drawbacks and the art has sought new and better methods for destroying toxic PCBs in soils, sediments and sludges.

SUMMARY OF THE INVENTION

It has now been discovered that PCBs are chemically degraded upon contact with a Lewis acid catalyst.

While the mechanism of the reaction is thought to be catalytic, the invention is not premised upon that mechanism and other mechanisms may account for the degradation reaction observed.

The degradation is performed in the presence of a cation which combines with the chloride ion liberated by the degradation of the PCBs to form a solid precipitate which can readily be removed. The process can be performed on PCBs in solution in a wide range of concentrations, including trace amounts, permitting full recovery of the bulk of the solution free of PCBs. The process may be incorporated in a batch, continuous, or semicontinuous process. Further features, advantages and embodiments of the invention will be evident from the description which follows.

DETAILED DESCRIPTION OF THE INVENTION AND PREFERRED EMBODIMENTS

Figure 1:
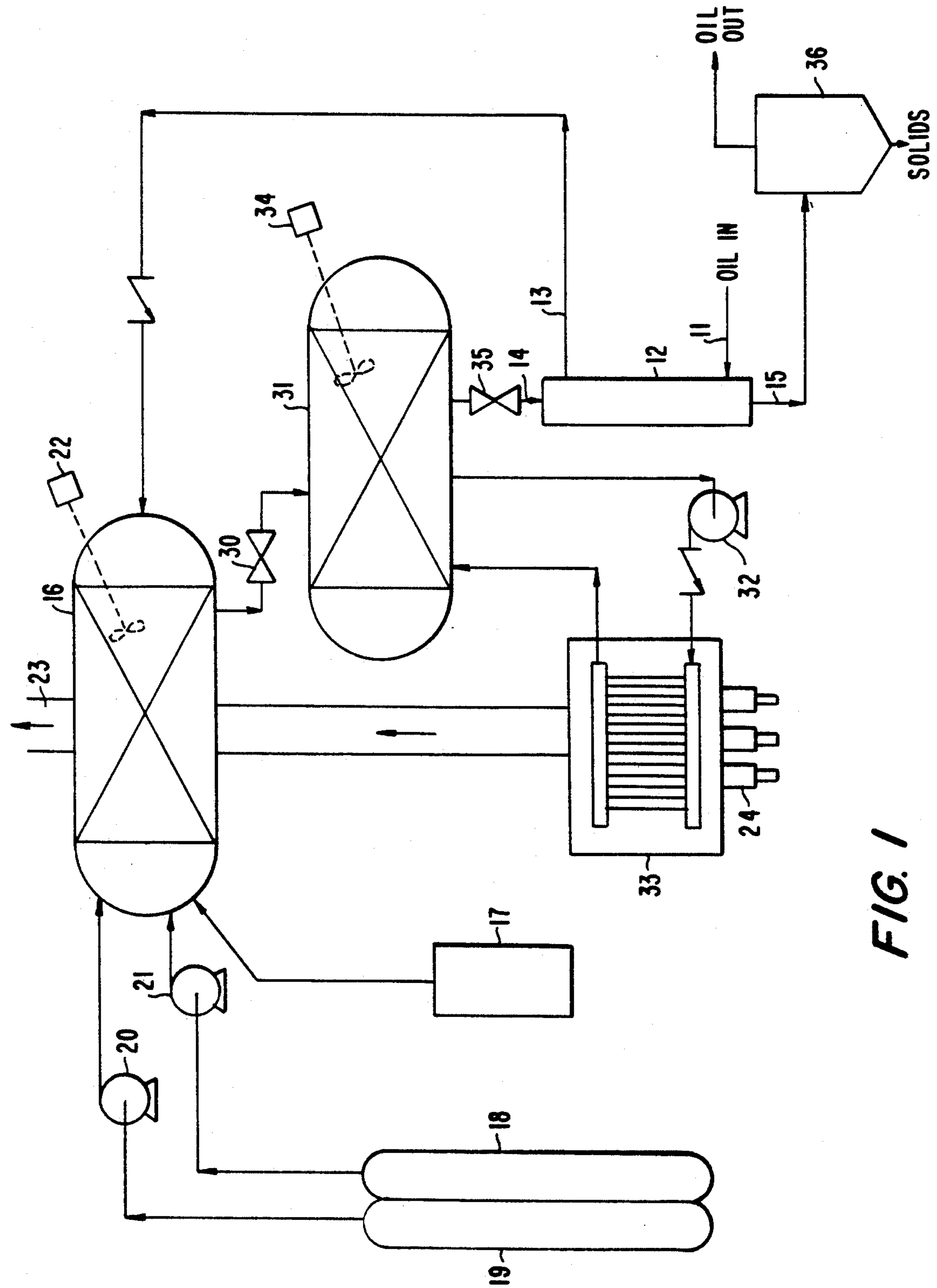
FIG. 1 is a flow diagram for a batchwise process in accordance with one embodiment of the present invention.

The term "Lewis acid" is used herein in accordance with its commonly accepted meaning in the chemical field, i.e., a molecule or ion which combines with a second molecule or ion by forming a covalent bond with two electrons from the latter. Preferred Lewis acids are metal halide-type Lewis acids, which have an electron-deficient central metal atom capable of electron acceptance. Among these, halides of aluminum, beryllium, cadmium, zinc, boron, gallium, titanium, zirconium, tin, antimony, bismuth, iron and uranium are preferred. The preferred halides are chlorides and bromides. Combinations of species are also included within the scope of the invention. Particularly preferred Lewis acids are aluminum and ferric halides, particularly aluminum and ferric chlorides ($AlCl_3$ and $FeCl_3$). In the most preferred embodiments of the invention, aluminum chloride and ferric chloride are used in combination. The Lewis acid must be used in anhydrous form.

The cation which combines with the liberated chloride ion to form a precipitate is preferably an alkali or alkaline earth metal ion. Particularly preferred metal ions are sodium, potassium and calcium, potassium being the most preferred. The cation may be added to the reaction medium in any form which will render it available for reaction with the chloride ion. For example, it may be introduced as a hydroxide, acetate, carbonate or alkoxide. The metal hydroxide is a particularly preferred form.

While the presence of the cation is eminently desirable in order to react with the halogen atoms, or more precisely, with hydrohalogen released from the degraded PCBs, the reaction can be carried out without such cations. The reaction's product so obtained is hydrohalogen which may be disposed of as known in the art.

Water enters the reaction system with contaminated fluid, may be disadvantageously added into the system with normally deliquescent alkali metal hydroxides, or be formed by the reaction of alkali metal hydroxide and alcohol. Steps as are further described below are taken to remove such water before processing.

Treatment of Nonaqueous Fluids

The process is applicable to PCBs present as contaminants in nonaqueous fluids, i.e., in concentrations as low as 10 ppm and preferably in from about 100 to about 10,000 ppm. The process of the invention requires a nonaqueous reaction medium. The process of the invention is advantageously used to detoxify organic liquids such as transformer oils. If water is present in the contaminated fluid, it must therefore be removed first, for example by vacuum dehydration or by stripping with a gas at elevated temperatures. If the fluid which is contaminated by the PCBs is water itself, the PCBs can be extracted with toluene to form a toluene solution of the PCBs. The toluene solution is then treated in accordance with the present invention.

Nonaqueous solvents which are miscible with the liquid medium containing the PCBs can be used to dissolve the Lewis acid catalyst and cation to facilitate their addition to the contaminated liquid. Low boiling solvents are preferred in view of the ease in which they can be evaporated from the reaction mixture prior to bringing the mixture up to reaction temperature. Particularly preferred solvents are alcohols, with methanol being a particularly convenient choice. The use of anhydrous aluminum chloride, ferric chloride dissolved in methanol, and potassium hydroxide dissolved in methanol, both of the latter in the highest concentration achievable, are particularly effective. As one example of the proportions which may be used, based on a 1000-gallon (3785-liter) quantity of contaminated oil containing 500 ppm PCBs, one may use 6 lbs (2.4 kg) of anhydrous $AlCl_3$, 1 gallon (3.785 liters) of a solution of 60% $FeCl_3$ dissolved in methanol, and 1.5 gallons (5.7 liters) of a solution of approximately 25% potassium hydroxide in methanol. Polyethylene glycol is an advantageous alcohol to use because water formed during reaction of alkali metal hydroxide and PEG may be boiled off at elevated temperatures without boiling off the PEG, thereby permitting the alcoholate, e.g., NaPEG or KPEG, to be introduced into the reaction system.

The Lewis acids may also be introduced into the PCB-containing organic liquid by corrosion of a metal vessel in which the organic liquid is contained. Corrosion of carbon steel or stainless steel pipes, valves, reaction vessels and the like, can provide adequate quantities of Lewis acid to cause the reaction to proceed and substantially quantitatively degrade the PCBs contained in the organic liquid.

The ratios may be varied widely, and are not critical. In general, however, best results will be achieved with a weight ratio of Lewis acid to PCBs ranging from about 0.5:1 to about 50:1, preferably from about 1:1 to about 20:1. When aluminum chloride and ferric chloride are used, the preferred ranges are from about 1:1 to about 10:1 for each. The cation which combines with the liberated chloride ion is generally used in excess. When the source of the cation is potassium hydroxide, best results are achieved when the latter is used at a weight ratio of from about 1:1 to about 20:1 with respect to the PCBs.

The reaction is conducted at elevated temperature, although the temperature itself is not critical and can vary widely. An appropriate temperature range will be high enough to provide a reaction rate which will achieve completion of the reaction within a reasonable, economically efficient period of time, yet not so high as to break down the Lewis acids or convert the desirable components of the contaminated medium in which the PCBs are contained. With these considerations in mind, reaction temperature will generally be at least about 100° C. For most systems, temperatures within the range of about 100° C. to about 500° C., preferably from about 300° C. to about 350° C., will provide the best results. The pressure may also vary widely. Atmospheric pressure is sufficient for most applications.

The reaction may be performed in either batchwise, continuous, or semicontinuous manner. In a batch process or the batch portion of a semicontinuous process, the reaction time will vary depending on the reaction conditions, the concentration of PCBs, and the ratios of system components. The appropriate length of time can be readily determined in each case by one skilled in the art using routine monitoring techniques, such as periodic sampling and analysis by chromatography. In general, at temperatures above 300° C., trace amounts of PCBs (on the order of 1000 ppm) will be completely degraded within about 2 hours.

Once the reaction is complete, any solids precipitating as a result of the reaction, particularly the chloride salts, are readily removed by conventional techniques such as, for example, filtration, decantation, and centrifugation.

As one example of a continuous process, the contamination liquid medium to be treated may be passed through a bed of solid particles containing the Lewis acid and a compound of the cation. In the alternative, the solid particles may consist of inert solid carrier materials supporting the active species, either by impregnation or surface coating. The bed may be a fixed or fluidized bed.

The Lewis acid and cation particles may be mixed together or separated into individual layers so that the contaminated liquid passes through them in sequence. In the latter case, it is preferred that the Lewis acid be contacted first, followed by the cation. When the Lewis acid is a combination of aluminum chloride and ferric chloride, it is further preferred that the aluminum chloride be the first layer contacted, followed by the ferric chloride. With layered beds, still better results are achieved using repeated sets of layers for the contaminated liquid to be passed through in succession. The contaminated liquid may also be continuously circulated through the mixed or layered bed for further reaction. The proportions of the various system components and the conditions of temperature and pressure described in connection with the batch process are applicable here as well.

A semicontinuous process arrangement may, for example, use alternating circulation loops in timed sequence. Such arrangements will be readily apparent to those skilled in the art.

Treatment of Soils

The invention is also advantageously applied to the detoxification of soils, sediments and sludges. The terms soils, sediments and sludges for and hereinafter "soils" (for purposes of brevity) have their art-accepted meanings. These soils may contain, among other contaminants including various organic liquids, PCBs and or PCBs dissolved in one or more organic liquids, e.g., transformer oils. The process of the invention can be used to remediate soils by contacting the soil under anhydrous conditions with an effective amount of a Lewis acid.

The Lewis acids, which include those described above, are preferably aluminum and ferric chlorides ($AlCl_3$ and $FeCl_3$) and combinations thereof. They may be introduced into the contaminated soil in an anhydrous organic liquid, e.g., methanol, as described above. Alternatively, the Lewis acids may be present, in situ, in the soil as a component thereof or may be formed in situ, and in such instance no external Lewis acid need be added. The Lewis acids may also be provided by forming them in situ by reaction of a metal, e.g., aluminum or iron, in the hydrohalogen or halogen-producing environment of the process system. Still further, as described above, the Lewis acids may be furnished to the process by corrosion of an interior surface of a vessel containing the PCB bearing soil. In such latter case, the Lewis acids are provided at no additional cost simply by the natural process of corrosion of the pipes, valves, mixers and reactors in which the contaminated soil is processed.

The process of the invention may be applied to soils containing even trace amounts of PCBs, i.e., in concentrations as low as 50 ppm. Typically, soils to be remediated by the process of the invention will contain PCBs in concentrations in the range of from 50 to 50,000 ppm and more usually in the range of 100 to 3000 ppm.

In the preferred embodiments of the invention, as applied to soils, the anhydrous PCB-containing soil, and this includes those instances where the PCB is dissolved within an organic liquid contained in the soil or is simply contained therein, is contacted with an effective amount of a metal halide Lewis acid and a metal cation capable of reacting with hydrohalogen released from the PCBs. The source of the metal cation may be the hydroxide, acetate, carbonate, or alkoxide, and preferably the source is the metal hydroxide. Alkali metal hydroxides are the most preferred.

It may be advantageous to introduce an organic liquid solvent into the PCB-containing soil or into soil containing PCB dissolved in another organic liquid. Introduction of an organic solvent together with the Lewis acid and the source of metal cation may facilitate solution of the PCB in the added solvent and/or may facilitate contact of the Lewis acid and metal cation with the PCB whether it is initially in a dissolved form or free within the soil. Polyethylene glycol (PEG) is an advantageous alcohol because it is environmentally innocuous when left within the remediated soil.

In a preferred embodiment the alkaline metal cation, in the form of a hydroxide, and an auxiliary solvent, e.g., polyethylene glycol (PEG) may be added together to the reaction mixture as separate components. These may perform their separate functions as described above, and/or may react in situ to form the so-called KPEG or NaPEG adducts which have been found to be effective PCB decomposition agents in Ptylewski, et al., U.S. Pat. No. 4,400,552 and other "KPEG" and "NaPEG" patents. These patents include U.S. Pat. Nos. 4,337,368, 4,349,380, 4,483,716, 4,417,977, 4,430,208, 4,471,143, 4,460,797, 4,602,994, and 4,523,043. The subject matter of Ptylewski, et al. U.S. Pat. No. 4,400,552 is incorporated herein. Alternatively, the adduct of the two compounds can be prepared and added to the reaction system where it serves as both a decomposition agent and as a source of cation.

The adduct is broadly a compound of the formula $$HO[-(\overset{R_1}{\underset{R_2}{C}})_z-]_n-R$$

wherein R is hydrogen or lower-alkyl, $R_1$ and $R_2$ are the same or different and are selected from the group consisting of hydrogen, lower alkyl, cycloalkyl having from 5 to 8 carbon atoms, and aryl, n has a value from about 2 to about 400, and z has a value of at least 2, which includes polyglycols and polyglycol monoalkyl ethers. The cycloalkyl radical may be cyclopentyl, cyclohexyl, cycloheptyl and cyclooctyl. The aryl radical may be phenyl, benzyl, biphenyl, naphthyl, etc. The substitutes on the $R_1$ and $R_2$ radicals include, but are not limited to lower-alkyl, e.g., methyl, ethyl, propyl, butyl, isobutyl, etc.; halo, e.g., chloro, bromo; nitro; sulfato; carboxyl; amino; mono-and di-lower-alkylamino, e.g., methylamino, ethylamino, dimethylamino, methylethylamino; amido; hydroxy; lower alkoxy, e.g., methoxy, ethoxy, etc.

Suitable reactants falling within the above formula include diethylene glycol, diethylene glycol monomethyl ether, polyether glycols, such as polyethylene glycols, polypropylene glycols, and polybutylene glycols and related long chain glycol monoalkyl ethers. The preferred reactants are those of the above general formula wherein $R_1$ and $R_2$ are hydrogen and z is 2. Particularly preferred are polyethylene glycols, i.e., polymers of the formula $HO-[CH_2-CH_2O-]H$, having an average molecular weight range from about 100 to about 20,000. The above-described reactants may be either liquids or solids. Those which are solids, e.g., the high molecular weight polyethylene glycols, should be melted before the reaction is begun. Neither low volatility, nonpolar liquids, nor glycolic liquids in which both terminal hydroxyl groups are alkylated has been found to produce the desired decompositions. The term "polyglycols," as used herein, is intended to signify polymers of dihydric alcohols.

The amount of Lewis acid used may be varied widely. It is not deemed to be critical. In general, best results will be achieved with a weight ratio of Lewis acid to PCBs ranging from about 0.5:1 to 50:1 and preferably from about 1:1 to 20:1.

The reaction is conducted at elevated temperature, although the temperature itself is not critical. Typically the temperature is from 220° C. to 500° C. and best results are obtained at temperatures in the range of from 280° C. to 350° C.

In treating soils, the contaminated soil may be introduced into a blender together with, e.g., alkali metal hydroxide, a solvent such as polyethylene glycol, and an easily volatilized dispersant, e.g., water (which is volatilized prior to treatment), to improve the dispersion of the components. After blending, the mixture is transferred to a rotary kiln wherein the water is removed by either vacuum dehydration or air stripping and then the degradation reaction carried out. The decontaminated soil is continuously removed from the rotary kiln. Other batch, semicontinuous or continuous processes will be apparent to those skilled in the art.

Turning now to the figures, FIG. 1 is a process flow diagram for a batch process version of the present invention.

Contaminated oil enters at an oil input 11 to a heat exchanger 12, which leaves through an oil exit line 13. In the heat exchanger 12, this feed oil is connected with and heated by hot oil emerging from the reaction zone. The latter (decontaminated) oil enters by a product oil inlet 14 and leaves by a product oil outlet 15 after having been cooled by the feed oil to a temperature of approximately 100° C. The feed oil is simultaneously heated to about 90° C.

The heated feed oil is then fed to a mixing vessel 16, where it is combined with anhydrous aluminum chloride supplied from a holding vessel 17, ferric chloride in methanol solution from a holding vessel 18, and potassium hydroxide in methanol solution from a holding vessel 19. The latter two, being in liquid form, are fed to the mixing vessel 16 through a dual pump 20, 21. The components are stirred in the mixing vessel 16 by a motorized agitator 22, and the temperature is raised by heat from the exhaust gases 23 from a series of burners 24 in a heating chamber used in a downstream section of the process. The reaction mixture is retained in the mixing vessel 16 until a temperature of approximately 250° C. is reached. For a 1000-gallon batch of contaminated oil, using approximately 1-2 gallons each of the two liquid additives and 5–10 lbs of the solid aluminum chloride, a residence time in the mixing vessel of about one-half hour will be sufficient.

Once the reaction mixture has reached the desired temperature in the mixing vessel 16, an exit valve 30 is opened, permitting passage of the reaction mixture into a reaction vessel 31. The reaction mixture is circulated from this reaction vessel 31 by way of a circulation pump 32 through a shell-and-tube heat exchanger 33, fired by the aforementioned burners 24, to slowly raise the temperature, typically approximately 322° C. A motorized agitator 34 continuously stirs the reaction mixture as it circulates to avoid uneven or excessive heating. The reaction mixture is retained in the reaction vessel 31 at the reaction temperature until the reaction is complete, typically about 1 to 2 hours for a 1000-gallon batch.

Once the reaction is complete, an exit valve 35 is opened, permitting the reaction mixture to pass through the aforementioned heat exchanger 12, to be cooled down which heating the incoming feed oil. The cooled down mixture is then passed to a separator 36, in which the salts settle out and the oil is removed by decantation. The spent salts include the potassium chloride precipitated as a result of the degradation of the PCBs, and may be flushed with water and discarded.

Figure 2:
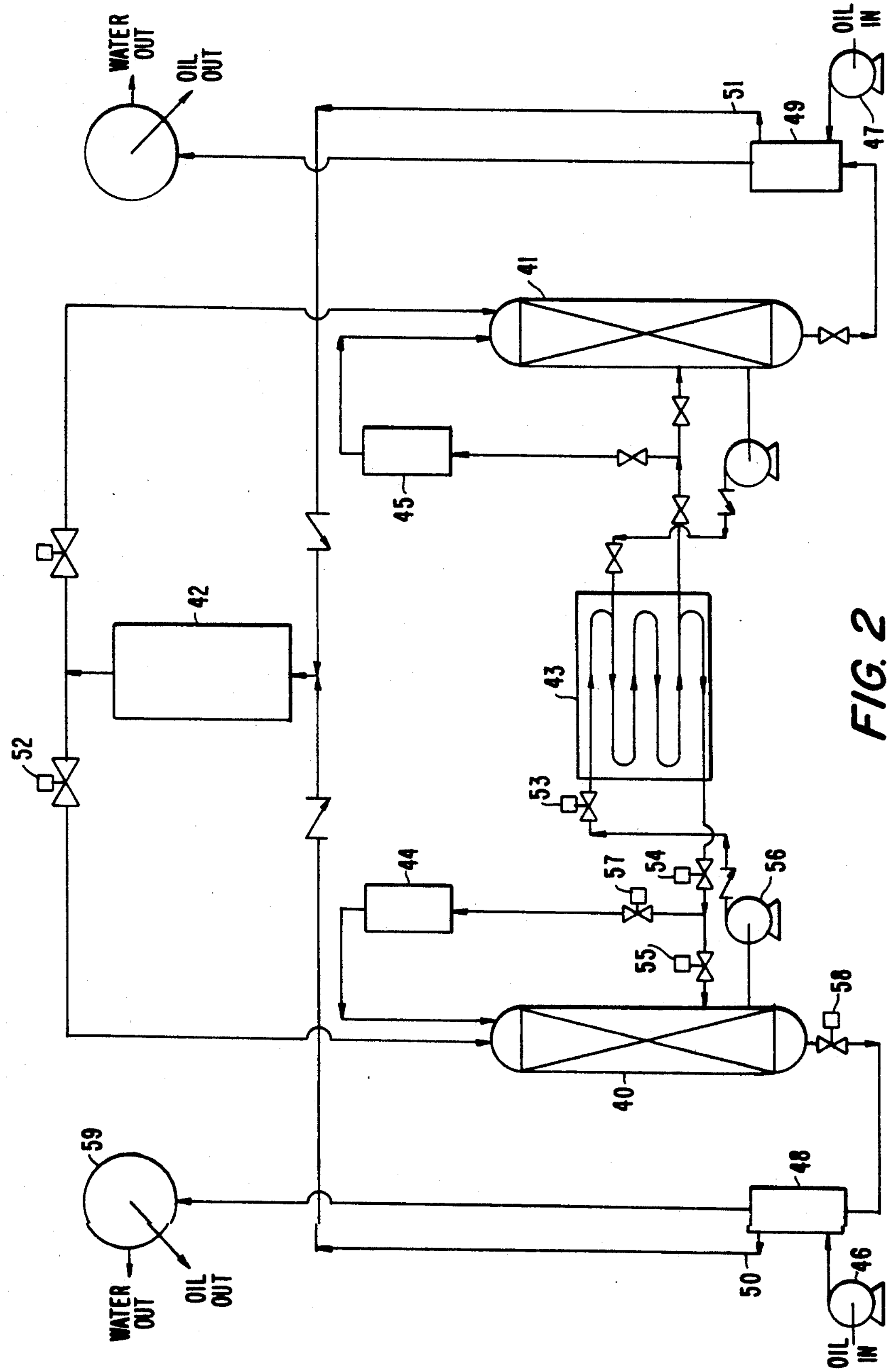
FIG. 2 is a flow diagram for a continuous process in accordance with a second embodiment of the present invention.

FIG. 2 depicts a process flow diagram for a semicontinuous or continuous batch process. This system has two reaction vessels 40, 41 for alternating use, utilizing a common preheat tank 42, with the contents of each reaction vessel further heated by circulation through a common heat exchanger 43. All three tanks are equipped with air relief valves. The Lewis acid and cation components of the system are used in this process in the form of beds of solid particles which the reaction mixture passes through. Two such beds 44, 45 are included, one for each of two reaction vessels 40, 41.

To begin a typical running sequence, the preheat tank 42 is filled with contaminated oil by either of two gear pumps 46, 47. To do this, these pumps direct the feed oil first to one of two heat exchangers 48, 49 which permits heat exchange with decontaminated product mixture in the same manner as the entering heat exchanger 12 of the batch process of FIG. 1. The heated oil emerges from the heat exchanger through an oil outlet line 50, 51 which feeds the oil to the preheat tank 42. This tank also serves as a storage tank for retaining a batch of contaminated oil while a previous batch is being treated.

The running sequence for reaction tank 40 may then be started by filling the reaction tank 40 with oil from the preheat tank 42 through valve 42, then opening valves 53, 54 and 55 and actuating a gear pump 56 which draws the reaction vessel contents out of the reaction vessel and circulates it through the heat exchanger 43. This circulation is continued until the desired temperature is reached. Valve 55 is then closed and valve 57 is opened, directing the contaminated oil through the catalyst bed 44. The reaction mixture thus circulates through both the heat exchanger 43 and the catalyst bed 44 for a sufficient period of time to achieve complete conversion of the PCBs.

The configuration of the catalyst bed, as indicated above, may assume any of a variety of forms. As one example, sequenced layers of aluminum chloride, ferric chloride, and potassium hydroxide in the form 16-mesh granules may be used, in layers one-half inch (1.3 cm) in depth, supported by 350-mesh stainless steel screens, leaving room for fluidization, typically one-quarter inch (0.64 cm) clearance above each layer. Several groups of these layers, such as for example 10 groups, may be used for efficiency. Circulation through the catalyst bed may be continued until the reaction is complete. As before, this is readily determined by routine monitoring. For a 1000-gallon batch, a typical circulation time will be 0.75 hour.

After the passage of a preselected period of time, the valves 55 and 57 are closed, the gear pump 56 is turned off, and the drain valve 58 is opened. This permits passage of the treated oil through the initial heat exchanger 48, where its temperature is lowered to approximately 100° C. Upon leaving this heat exchanger, the cooled oil is fed to a separator 59, which functions in the same manner as the separator 36 of the batch process of FIG. 1, including the use of water to rinse the potassium chloride before the latter is discarded. In a preferred use of this embodiment, valves 52, 53, 54 and 58 are electrically controlled valves and valves 55 and 57 are thermally controlled.

The corresponding valves and gear pump in association with the second reaction vessel 41 are then energized in the same sequence. This can be done during draining of the first reaction vessel simultaneously with the heating of feed oil through the initial heat exchanger 48 and in the preheat tank 42.

Figure 3:
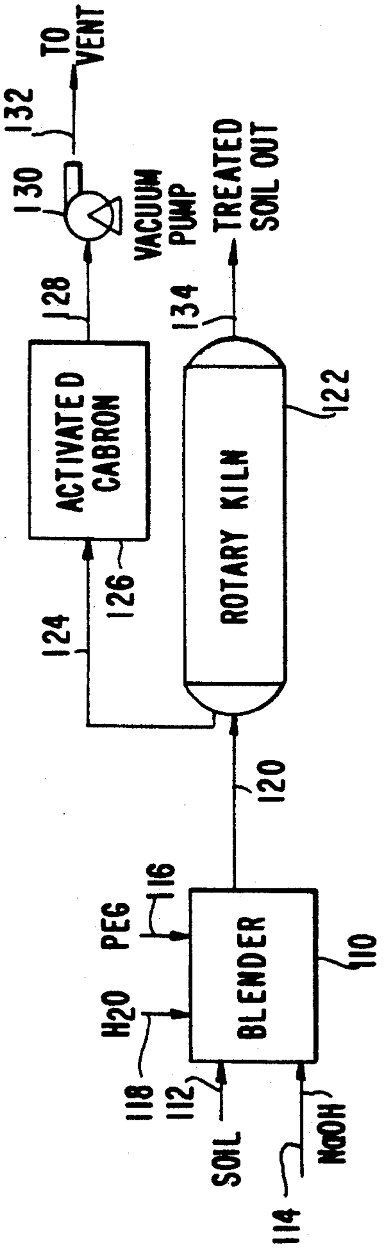
FIG. 3 is a flow diagram for a continuous process for the remediation of PCB-containing soils, sediments and sludges.

FIG. 3 depicts a continuous process diagram for the treatment of PCB-contaminated soils, sediments or sludges. The process scheme of FIG. 3 is employed as described below in Examples III and IV. Reference numeral 110 refers to a blender into which contaminated soil is introduced via conduit 112, sodium hydroxide is introduced via conduit 114, polyethyleneglycol is introduced via conduit 116 and water is introduced via conduit 118. The added components are mixed and blended in blender 110 and pass via conduit 120 to rotary kiln 122. Therein the blended soil and other components are heated via heating means (not shown) and subjected to heat and vacuum dehydration. A water vapor stream containing some organic liquid components is drawn off via conduit 124 and passes through activated carbon bed 126 and then through conduit 128 to vacuum pump 130 and is exhausted to the atmosphere via conduit 132. Any organic components, including PCBs, are removed in activated carbon bed 126.

The materials remain in rotary kiln 122 for a time sufficient to cause the degradation of the PCBs contained therein. The Lewis acid is provided by the adventitious corrosion of any or all of blender 110, conduit 112, conduit 120, or rotary kiln 122, which are exposed to wet PCB-containing soil. After the PCBs in the soil have been degraded in rotary kiln 122, the clean soil is removed via conduit 134.

The following examples are offered for purposes of illustration, and are intended neither to define nor limit the invention in any manner.

EXAMPLE I

A reaction vessel was charged with 300 ml by weight of transformer oil, Univolt N-61, obtained from Exxon, St. Paul, Minn., spiked with approximately 500 ppm of Aroclor 1260, a polychlorinated biphenyl obtained from National Electric, St. Paul, Minn. 5 grams $AlCl_3$, 1.5 grams $FeCl_3$, and 0.5 gram of a 25% solution of KOH in methanol.

The mixture was gradually heated and agitated until the methanol had been evaporated. The mixture was then brought to a temperature of 325° C. and held at this temperature for 1.5–2 hours. Samples were drawn periodically and analyzed by chromatography. At the end of the time period indicated above, the chromatogram showed a complete absence of PCBs.

It was noted during the reaction that no distillates other than the methanol were collected. The lighter hydrocarbons in the transformer oil merely refluxed. PCB analysis was done by ASTM method D-4059, using packed column gas chromatography and an electron capture detector, yielding a final result of less than 1 ppm PCBs.

EXAMPLE II

Three hundred millimeters of mineral oil containing 52% Aroclor 1260, 5 grams of aluminum shavings and 0.01 ppm of $AlCl_3$ were heated in a glass flask in a sand bath to 320° C. and held at that temperature for two hours. Vapor from the flask is scrubbed in an aqueous NaOH.

After cooling, analysis indicates a PCB content of 4 ppm. The aluminum shavings are observed to be substantially corroded and reacted. This example illustrates catalysis by $AlCl_3$ formed in situ.

EXAMPLE III

Soil with a moisture content of fifteen percent (15%) by weight containing 1740 ppm of PCBs, as determined by hexane extraction followed by GC/MS, is mixed with PEG 350, and NaOH. Additional water is added as a dispersing agent, to produce a treatment feed stream having the following component flows and composition:

| | |
|---|---|
| Soil (dry basis) | 2000 #/hr. |
| PCB Content | 1740 ppm. based on soil |
| Total water | 900 #/hr. |
| NaOH (100% basis) | 100 #/hr. |
| PEG | 20 #/hr. |

The above mixture is fed continuously to a carbon steel rotary kiln 3 ft. in diameter and 38 ft. long. Reaction temperature is 300° C. Pressure is maintained just below atmospheric to prevent leakage of PCB-containing vapors through the seals. Evaporation of the moisture proceeds rapidly at these conditions and the vapor is removed and treated with activated carbon before being exhausted through a vacuum pump.

Average residence time in the reactor is 1 hr. Analysis of the soil discharged indicates a PCB content of 1.99 ppm. Soluble iron content of the soil is found to be 135 ppm. This example illustrates effective catalytic degradation of PCBs by iron chloride generated by reactor corrosion.

EXAMPLE IV

Example IV is repeated using a 316 L SS reactor. Substantially identical results are obtained. This illustrates that the corrosion rates of carbon steel and stainless steel are similar in chloride systems.

The foregoing is offered primarily for purpose of illustration. It will be readily apparent to those skilled in the art that the various elements of the process as well as materials and equipment described for use herein in connection with the invention may be further varied, modified or substituted without departing from the spirit and scope of the invention.

WHAT IS CLAIMED IS:

1. A process for degrading polychlorinated biphenyls in a nonaqueous liquid medium, said process comprising contacting said medium under substantially anhydrous conditions with a catalytic amount of a Lewis acid catalyst in the presence of a cation which combines with chlorine to form a solid precipitate in said nonaqueous medium at an elevated temperature, to precipitate at least a substantial portion of the chlorine in said polychlorinated biphenyls as the chloride salt of said cation.

2. A process in accordance with claim 1 in which said Lewis acid catalyst is a metal halide selected from the group consisting of aluminum, beryllium, cadmium, zinc, boron, gallium, titanium, zirconium, tin, antimony, bismuth, iron and uranium halides and combinations thereof.

3. A process in accordance with claim 2 in which said metal halide is a member selected from the group consisting of aluminum and ferric halides and combinations thereof.

4. A process in accordance with claim 1 in which said cation is a metal ion selected from the group consisting of alkali and alkaline earth metal ions.

5. A process in accordance with claim 1 in which said cation is a metal ion selected from the group consisting of sodium, potassium and calcium.

6. A process in accordance with claim 1 in which said elevated temperature is from about 100° C. to about 500° C.

7. A process in accordance with claim 1 in which said elevated temperature is from about 300° C. to about 350° C.

8. A process in accordance with claim 1 in which the weight ratio of said Lewis acid catalyst to said polychlorinated biphenyl is from about 0.5:1 to about 50:1.

9. A process in accordance with claim 1 in which the weight ratio of said Lewis acid catalyst to said polychlorinated biphenyl is from about 1:1 to about 20:1.

10. A process in accordance with claim 1 in which said cation is present in sufficient quantity to precipitate substantially all of the chlorine in said polychlorinated biphenyls.

11. A process in accordance with claim 1 comprising passing said nonaqueous liquid medium through a bed of solid particles containing said Lewis acid catalyst and a compound of said cation.

12. A process in accordance with claim 11 in which said Lewis acid catalyst and said compound of said cation are separated into individual layers in said bed.

13. A process for degrading polychlorinated biphenyls in a nonaqueous liquid medium, said process comprising passing said nonaqueous liquid medium through a bed of solid particles, said bed divided into a first layer comprising aluminum chloride, a second layer comprising ferric chloride, and a third layer comprising potassium hydroxide, at a temperature of at least about 100° C.

14. A process for degrading polychlorinated biphenyls in a nonaqueous liquid medium, said process comprising contacting said medium under anhydrous conditions with a metal halide Lewis acid in the presence of a metal hydroxide in alcohol solution, the metal of which metal hydroxide combines with chlorine to form a solid precipitate in said nonaqueous medium at an elevated temperature, to precipitate at least a substantial portion of the chlorine in said polychlorinated biphenyls as the chloride salt of said cation.

15. A process for degrading polychlorinated biphenyls in a nonaqueous liquid medium, said process comprising contacting said medium under substantially anhydrous conditions with aluminum chloride and ferric chloride in the presence of potassium hydroxide in alcohol solution at an elevated temperature to precipitate at least a substantial portion of the chlorine in said polychlorinated biphenyls as potassium chloride.

16. A process in accordance with claim 15 in which said Lewis acid is comprised of a combination of aluminum chloride and ferric chloride, each at a weight ratio of from about 1:1 to about 10:1 with respect to said polychlorinated biphenyls, and said metal hydroxide is potassium hydroxide at a weight ratio of from about 1:1 to about 20:1 with respect to said polychlorinated biphenyls.

17. A process for degrading PCBs contained in an organic liquid, comprising contacting said liquid under anhydrous conditions with an effective amount of a metal halide Lewis acid.

18. A process as recited in claim 17 wherein said metal halide Lewis acid comprises aluminum chloride, ferric chloride, or mixtures thereof.

19. A process as recited in claim 17 wherein said metal halide Lewis acid is furnished to said process by corrosion of an interior surface of a vessel containing said organic liquid.

20. A process for dehydrohalogenating PCBs contained in trace amounts in an organic liquid, comprising contacting said liquid under anhydrous conditions with an effective amount of a metal halide Lewis acid.

21. A process as recited in claim 20 wherein said organic liquid is a transformer oil.

22. A process for degrading PCBs contained in an organic liquid, comprising contacting said liquid under anhydrous conditions with (a) an effective amount of a metal halide Lewis acid, and (b) a metal cation capable of combining with halogen released from said PCBs.

23. A process as recited in claim 22 wherein said metal halide Lewis acid is aluminum chloride, ferric chloride or mixtures thereof.

24. A process as recited in claim 22 wherein said metal halide Lewis acid is furnished to said process by corrosion of an interior surface of a vessel containing said organic liquid.

25. A process as recited in claim 22 wherein said metal cation is added to said process as an alkali or alkaline earth metal hydroxide, alkoxide, acetate or carbonate.

26. A process for dehydrohalogenating PCBs contained in trace amounts in an organic liquid comprising contacting said liquid under anhydrous conditions with an effective amount of (a) a metal halide Lewis acid, and (b) a metal cation capable of reacting with hydrohalogen released from said PCBs.

27. A process as recited in claim 26 wherein said organic liquid is a transformer oil.

28. A process for catalytically degrading PCBs in an organic liquid, comprising contacting said liquid under anhydrous conditions with a catalytically effective amount of a catalyst comprising a metal halide Lewis acid.

29. A process as recited in claim 28 wherein said metal halide Lewis acid comprises aluminum chloride, ferric chloride, or mixtures thereof and said metal halide Lewis acid is furnished to said process by corrosion of an interior surface of a vessel containing said liquid.

30. A process for catalytically dehydrohalogenating PCBs contained in trace amounts in an organic liquid, comprising contacting said liquid under anhydrous conditions with a catalytically effective amount of a catalyst comprising a metal halide Lewis acid.

31. A process for catalytically degrading PCBs in an organic liquid, comprising contacting said liquid under anhydrous conditions with (a) a catalytically effective amount of a catalyst comprising a metal halide Lewis acid, and (b) a metal cation capable of combining with halogen released from said PCBs.

32. A process as recited in claim 31 wherein said metal halide Lewis acid comprises aluminum chloride, ferric chloride, or mixtures thereof.

33. A process as recited in claim 31 wherein said metal halide Lewis acid is furnished to said process by corrosion of an interior surface of a vessel containing said liquid.

34. A process as recited in claim 31 wherein said metal cation is added to said process as an alkali or alkaline earth metal hydroxide, alkoxide, acetate or carbonate.

35. A process for catalytically dehydrohalogenating PCBs contained in trace amounts in an organic liquid comprising contacting said liquid under anhydrous conditions with (a) a catalytically effective amount of a catalyst comprising a metal halide Lewis acid, and (b) a metal cation capable of combining with hydrohalogen released from said PCBs.

36. A process for the detoxification of soils, sediments and sludges containing an organic liquid having trace amounts of PCBs dissolved therein, comprising the steps of (a) removing water from said soil, sediment or sludge and from the organic liquid contained therein; and (b) contacting said liquid, under anhydrous conditions, with an effective amount of a metal halide Lewis acid.

37. A process as recited in claim 36 wherein said metal halide Lewis acid comprises aluminum chloride, ferric chloride, or mixtures thereof and said Lewis acid is furnished to said process by corrosion of an interior surface of a vessel containing said organic liquid.

38. A process as recited in claim 36 wherein said metal halide Lewis acid is contained in said soil, sediment, or sludge.

39. A process for the detoxification of soils, sediments and sludges containing an organic liquid having trace amounts of PCBs dissolved therein, comprising the steps of:

(a) removing water from said soil, sediment or sludge and from the organic liquid contained therein; and (b) contacting the said organic liquid with an effective amount of (i) a metal halide Lewis acid, and (ii) a metal cation capable of combining with halogen released from said PCBs.

40. A process as recited in claim 39 wherein said metal halide Lewis acid comprises aluminum chloride, ferric chloride, or mixtures thereof, and said Lewis acid is furnished to said process by corrosion of an interior surface of a vessel containing said organic liquid.

41. A process as recited in claim 39 wherein said metal cation is added to said process as an alkali or alkaline earth metal hydroxide, alkoxide, acetate or carbonate.

42. A process for the detoxification of soils, sediments and sludges containing trace amounts of PCBs, comprising the steps of (a) removing water from said soil, sediment or sludge; and (b) contacting said soil, sediment or sludge under anhydrous conditions, with an effective amount of a metal halide Lewis acid.

43. A process as recited in claim 42 wherein an organic liquid is introduced into said soil, sediment or sludge prior to contacting it with said Lewis acid.

44. A process as recited in claim 42 wherein said water is removed from said soil, sediment or sludge by stripping at elevated temperature.

* * * * *